United States Patent [19]

Iqbal et al.

[11] 4,349,671

[45] Sep. 14, 1982

[54] PROCESS FOR THE PRODUCTION OF METAL COMPLEXES OF ISOINDOLINE AZINES

[75] Inventors: Abul Iqbal, Ettingen; Paul Lienhard, Frenkendorf, both of Switzerland

[73] Assignee: Ciba-Geigy Corporation, Ardsley, N.Y.

[21] Appl. No.: 241,141

[22] Filed: Mar. 5, 1981

[30] Foreign Application Priority Data

Mar. 13, 1980 [CH] Switzerland ........................ 1975/80

[51] Int. Cl.$^3$ ............................................ C07D 403/14

[52] U.S. Cl. ................................ 542/417; 260/326.1; 544/225; 546/6; 546/7; 548/105; 548/106

[58] Field of Search ................ 542/417; 548/105, 106; 260/326.1; 544/225; 546/6, 7

[56] References Cited

U.S. PATENT DOCUMENTS 3,974,149 8/1976 L'Eplattenier ...................... 542/417
4,024,132 5/1977 L'Eplattenier ...................... 542/417
4,065,481 12/1977 L'Eplattenier ...................... 542/417
4,111,947 9/1978 L'Eplattenier ...................... 542/417

*Primary Examiner*—Arthur P. Demers
*Attorney, Agent, or Firm*—Luther A. R. Hall

[57] ABSTRACT

The invention relates to a process for the manufacture of 1:1 metal complexes of azines of the formula

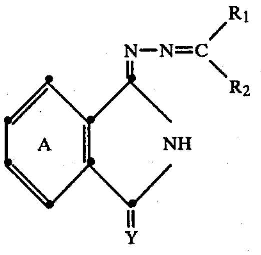

(I)

wherein $R_1$ is a hydrogen atom, an alkyl or aryl group, $R_2$ is an isocyclic or heterocyclic radical containing a hydroxyl or mercapto group adjacent to the azomethine group, Y is the radical of a compound which contains active methylene groups, or of an aryl or heteroaryl amine, and the ring A can contain substituents that do not confer solubility in water, which process comprises reacting a compound of the formula

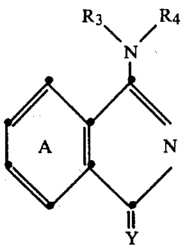

(II)

wherein $R_3$ is a hydrogen atom or an alkyl radical, $R_4$ is an alkyl, aryl or heteroaryl radical or the radical of the formula

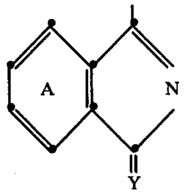

or $R_3$ and $R_4$, together with the nitrogen atom to which they are attached, form a 5- or 6-membered heterocyclic ring, and Y has the given meaning, with a hydrazone of the formula

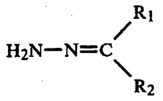

(III)

in the presence of a transition metal donor and in a polar organic solvent, at temperatures above 100° C.

Compared with pigments obtained by the prior art methods, the pigments of this invention have greater purity and better fastness properties, especially better fastness to migration, overspraying, light, atmospheric influences and heat.

9 Claims, No Drawings

PROCESS FOR THE PRODUCTION OF METAL COMPLEXES OF ISOINDOLINE AZINES

U.S. Pat. Nos. 4,022,770 and 4,111,947 describes the production of azines of the formula

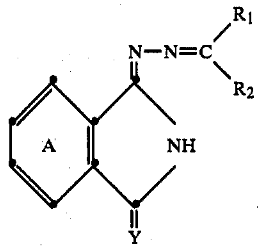
(I)

wherein $R_1$ is a hydrogen atom, an alkyl or aryl group, $R_2$ is an isocyclic or heterocyclic radical containing a hydroxyl or mercapto group adjacent to the azomethine group, Y is the radical of a compound which contains active methylene groups, or of an aryl or heteroaryl amine, and the ring A can contain substituents that do not confer solubility in water, by condensing a compound of the formula

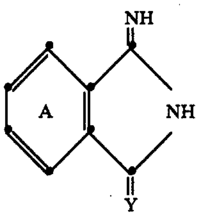
(Ia)

with a hydrazone of the formula

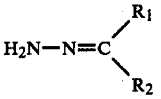
(III)

Although the compound of the formula (I) is obtained in good yield, the 1:1 nickel complexes obtained therefrom color plastics and lacquers in shades of unsatisfactory purity with inadequate fastness properties. The condensation of the compound of the formula (Ia) with the hydrazone of the formula (III) in the presence of nickel salts also does not produce satisfactory results.

It has now been found that the 1:1 metal complexes of azines of the formula (I) are obtained in excellent yield and purity by reacting a compound of the formula

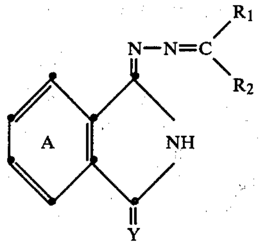
(I)

wherein $R_3$ is a hydrogen atom or an alkyl radical, $R_4$ is an alkyl, aryl or heteroaryl radical or the radial of the formula

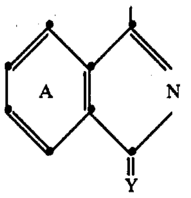
(IIa)

or $R_3$ and $R_4$, together with the nitrogen atom to which they are attached, form a 5- or 6-membered heterocyclic ring, and Y has the given meaning, with a hydrazone of the formula

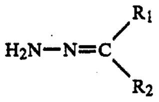
(III)

in the presence of a transition metal donor and in a polar organic solvent, at temperatures above 100° C.

The starting aminoisoindolenines of the formula (II) can be substituted in the benzene ring A by halogen atoms, for example 2 to 4 chlorine atoms, 1 to 2 alkyl or alkoxy groups, each of 1 to 4 carbon atoms, a phenyl, phenoxy or nitro group, an alkanoylamino group of 2 to 6 carbon atoms or a benzoylamino group. Preferably, however, the benzene ring A is unsubstituted.

Y is preferably a methine radical of the formula

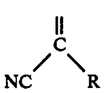

wherein R is a cyano group, an alkoxycarbonyl, alkylcarbamoyl or alkanoyl group of 2 to 6 carbon atoms, a benzoyl, carbamoyl, thiocarbamoyl or sulfamoyl group, a benzylcarbamoyl group, a phenylsulfamoyl or phenylsulfonyl group which is unsubstituted or substituted by halogen atoms or alkyl groups of 1 to 4 carbon atoms, but is especially a group of the formula

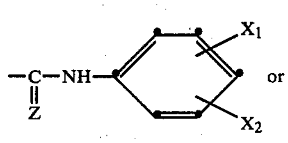
or
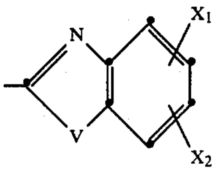

wherein Z is an oxygen or a sulfur atom, $X_1$ is a hydrogen, chlorine or bromine atom, a nitro, trifluoromethyl, carbamoyl or sulfamoyl group, an alkyl, alkoxy or alkylsulfamoyl group of 1 to 4 carbon atoms, an alkanoylamino, alkylcarbamoyl or alkoxycarbonyl group of 2 to 6 carbon atoms, a phenoxy, phenylcarbamoyl or phenylsulfamoyl group which is unsubstituted or substituted by chlorine or bromine atoms or methyl groups, and $X_2$ is a hydrogen, chlorine or bromine atom, an alkyl or alkoxy group of 1 to 4 carbon atoms, and V is O, S, or NH.

If $R_3$ is a hydrogen atom, the compound of the formula (II) can also have the tautomeric isoindoline form.

Alkyl radicals $R_3$ and $R_4$ preferably contain 1 to 6 carbon atoms and an aryl radical $R_4$ is preferably a phenyl radical which can be substituted by chlorine atoms or alkyl or alkoxy groups of 1 to 4 carbon atoms.

The compound of the formula (II) is obtained by known methods by condensing an aminoisoindolenine of the formula

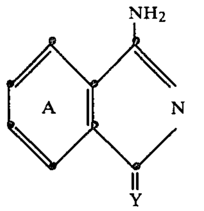
(V)

with an amine of the formula $HNR_3R_4$.

Examples of amines are: alkylamines such as methylamine, ethylamine, n-propylamine, isopropylamine, n-butylamine, n-hexylamine, n-octylamine, n-decylamine or laurylamine.

Aromatic amines are preferred, especially aminobenzenes of the formula

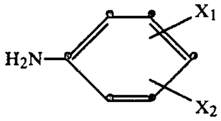

wherein $X_1$ and $X_2$ have the above meanings.

Representative examples of heterocyclic amines are those listed on columns 5-6 of U.S. Pat. Nos. 4,022,770 and 4,111,947, as well as 2-aminopyridine, 2-amino-5-chloropyridine, 2-amino-4-hydroxyquinoline and 2-amino-4,5-dimethylthiazole.

Representative examples of amines of the formula $HNR_3R_4$, wherein $R_3$ and $R_4$, together with the nitrogen atom to which they are attached, from a 5- or 6-membered heterocyclic ring, are: pyrrolidine, morpholine, piperidine etc.

As the amine radical is split off during the condensation, it is advisable to use as inexpensive amines as possible.

The compound of the formula (V) is obtained by condensing the corresponding 1-amino-3-iminoisoindolenine with an amine or a compound containing active methylene groups, especially one of the formula $NCCH_2R$, wherein R is as defined above.

Examples of such compounds are the acetonitriles listed on columns 6-7 of U.S. Pat. Nos. 4,022,770 and 4,111,947, as well as cyanoaceto-o-chlorophenyl-, p-chlorophenyl-, -m-chloropenyl-, -m-methylphenyl-, -p-methylphenyl-, -3,4-dichlorophenyl-, -3,5-dimethylphenyl-, -3,4-dimethylphenyl-, -3-chloro-4-methylphenyl-, -o-methoxyphenyl-, -2,4-dimethoxyphenyl-, -2,5-dimethoxyphenyl-, -p-acetylamino-phenyl-, -p-benzoylaminophenyl-, -3-chloro-4-p-chlorbenzoylaminophenyl-, -4-carbamoylphenyl-, -4-sulfamoylphenyl-, -4-phenylazophenyl-, -4-phenoxyphenyl-, -p-nitrophenyl-, -3-trifluoromethylphenyl-, or -2-chloro-5-trifluoromethylphenylamides, -2-cyanomethyl-4-phenyl-, -4-p-nitrophenyl-, -4-fluorophenyl- or -4-methylphenylthiazole.

Suitable compounds containing active methylene groups are also heterocyclic compounds which contain an active methylene group in the heterocyclic ring, for example those listed on column 7 of U.S. Pat. Nos. 4,022,770 and 4,111,947, e.g. 2,4-dihydroxyquinoline, 1-p-chlorophenyl-3-methyl-5-pyrazolone, 1-p-methylphenyl-3-methyl-5-pyrazolone, 1-phenyl-3-dichlorovinyl-5-pyrazolone, 1-p-methylphenyl-3-dichlorovinyl-5-pyrazolone.

Examples of amines which donate the radical Y are aromatic, but especially heterocyclic, amines, preferably those in which the amino group is present direct at 5- to 6-membered heterocylic ring which can contain 1 to 3 nitrogen atoms and, in addition, oxygen and sulfur atoms. An unsubstituted or substituted benzene nucleus can be fused to the heterocyclic parent nucleus. Examples of such amines are those listed on columns 5-6 of U.S. Pat. Nos. 4,022,770 and 4,111,947, and, in addition, 2-aminopyridine, diaminophthalazine, 2-amino-4-hydroxyquinoline, 2,6-diaminopyridine, 2-amino-4,5-dimethylthiazole.

In the hydrazones of the formula (III), $R_1$ is e.g. a phenyl radical, but preferably a hydrogen atom or an alkyl group of 1 to 4 carbon atoms, preferably the methyl group. If $R_2$ is an isocyclic radical, then it is e.g. a phenyl or naphthyl radical, but preferably a mono- or binuclear heterocyclic ring.

The hydrazones of the formula (III) are obtained by known methods, by reacting an oxo compound of the formula

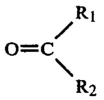

or the aldimine thereof, with hydrazine hydrate. Of particular intereset are aldehydes or ketones of the formula

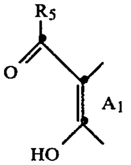

wherein $R_5$ is a hydrogen atom or a methyl group, $A_1$ is a naphthalene radical or a 5- or 6-membered heterocyclic ring which contains an oxygen, a sulfur or, in particular, a nitrogen atom in the $\alpha$- or $\gamma$- position to the carbon atom at which the hydroxyl group is located, and may additionally contain a further nitrogen atom in the ring and a fused benzene ring and/or a further heterocyclic ring.

Preferred oxo compounds are those of the formula

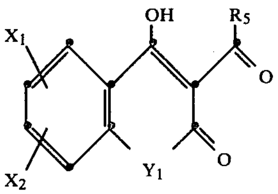

wherein $R_5$, $X_1$ and $X_2$ have the meanings assigned to them above and $Y_1$ is an oxygen or a sulfur atom or a NH group.

Particularly interesting compounds are also those of the formula

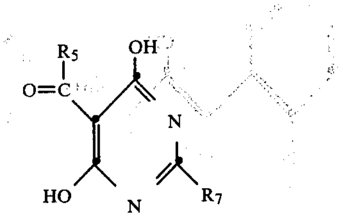

wherein $R_5$ has the indicated meaning, $R_6$ is a cyano, alkoxycarbonyl or carbamoyl group, and $R_7$ is a hydrogen atom, an alkyl, aryl or hydroxyl group; or those of the formula

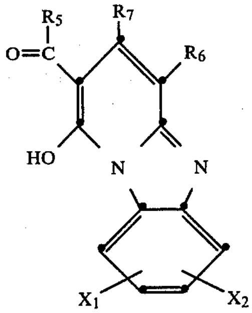

wherein $X_1$, $X_2$, $R_5$, $R_6$ and $R_7$ have the meanings assigned to them above; or those of the formula

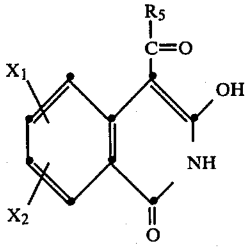

wherein $X_1$, $X_2$ and $R_5$ have the above meanings, and also hydroxynaphthaldehydes of the formula

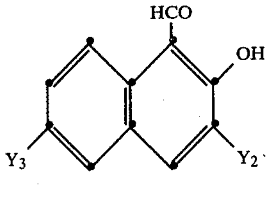

wherein $Y_2$ is a hydrogen atom, a carboxyl or carbamoyl group, an alkoxycarbonyl or alkylcarbamoyl group containing 2 to 6 carbon atoms, a phenylcarbamoyl group which is unsubstituted or substituted in the phenyl moiety by halogen atoms or alkyl or alkoxy groups containing 1 to 4 carbon atoms, $Y_3$ is a hydrogen or halogen atom, a methoxy, nitro or cyano group; or pyrazoles of the formula

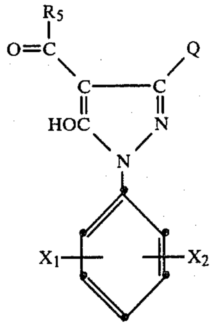

wherein $R_5$, $X_1$ and $X_2$ are as defined above and Q is a methyl group or an alkoxycarbonyl group containing 2 to 5 carbon atoms or a carbamoyl group.

Representative examples are the aldehydes and ketones listed in columns 10-11 of U.S. Pat. Nos. 4,022,770 and 4,111,947.

As metal donors it is preferred to use the salts of zinc, cadmium, manganese, cobalt, iron, and especially of copper and nickel, and mixtures of such metals. It is preferred to use the formates, acetates or stearates of these metals.

The reaction of the aminoindolenine of the formula (II) with the hydrazone of the formula (III) is conducted in a polar solvent, especially a hydrophilic polar solvent, for example an amide such as dimethyl formamide, formamide, dimethyl acetamide or N-methylpyrrolidone, and also dimethyl sulfoxide, acetonitrile or an alcohol, for example ethyl cellosolve. It is also possible to use a mixture of polar solvents. The reaction temperature is advantageously in the range from 100°-200° C.

The metal complex is isolated in conventional manner by filtration. The filter cake is washed thoroughly with solvent. The product is obtained in excellent yield and purity and can be used, without further purification, in finely dispersed form for coloring organic material of high molecular weight, e.g. cellulose ethers and esters, such as ethyl cellulose, acetyl cellulose, nitrocellulose, polyamide and polyurethanes, or polyesters, natural resins or synthetic resins, e.g. aminoplasts, especially urea-formaldehyde and melamine-formaldehyde resins, alkyd resins, phenolic plastics, polycarbonates, polyolefins such as polystyrene, polyvinyl chloride, polyethylene, polypropylene, polyacrylonitrile, polyacrylates, thermoplastics or curable acrylic resins, rubber, casein, silicone and silicone resins, singly or in mixtures. The specified materials of high molecular weight can be in the form of plastics, melts or of spinning solutions, lacquers or printing inks. Depending on the end-use, it is advantageous to use the pigments of the present invention as toners or in the form of preparations.

The pigment can be used in the form in which it is obtained in the synthesis or in slightly ground form to give opaque colorations. However, it can also be more thoroughly ground to give transparent colorations, for example strong metal effect finishes.

Mill base formulations in lacquers have advantageous flow properties.

The colorations obtained e.g. in plastics, filaments and lacquers, have high colour strength, excellent purity of shade, good dispersibility, good fastness to overspraying, migration, heat, light and migration as well as good gloss. Compared with the pigments obtained by the process of U.S. Pat. Nos. 4,022,770 and 4,111,947, the pigments of this invention have greater purity and better fastness properties, especially better fastness to migration, overspraying, light, atmospheric influences and heat.

The invention is illustrated by the following Examples.

EXAMPLE 1

0.65 g (0.003 mole) of 3-acetyl-2,4-dihydroxyquinoline hydrazone (prepared by reacting 3-acetyl-2,4-dihydroxyquinoline with hydrazine hydrate in boiling ethanol) and 0.78 g (0.00315 mole) of nickel acetate tetrahydrate are dissolved in 40 ml of N-methylpyrrolidone and the solution is heated to 60° C. Then 1.2 g (0.003 mole) of 1-(cyanobenzimidazolylmethylene)-3-N-p-nitrophenyliminoisoindoline (prepared by reacting 1-(cyanobenzimidazolylmethylene)-3-iminoisoindoline with p-nitroaniline in dimethyl formamide) are added and the mixture is stirred for ½ hour at 150°-155° C. and filtered hot (80° C.). The filter cake is washed with N-methylpyrrolidone and ethanol and dried in vacuo at 80° C., affording 1.5 g (92.3% of theory) of a red metal complex of the composition $C_{28}H_{17}N_7O_2Ni$ and having the formula

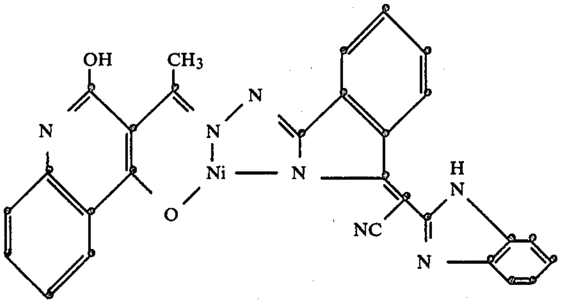

| Microanalysis: $C_{28}H_{17}N_7O_2Ni$ (molecular weight 542.20) | C | H | N | Ni |
|---|---|---|---|---|
| % calculated: | 62.03 | 3.16 | 18.08 | 10.83 |
| % found: | 62.10 | 3.20 | 18.30 | 10.80 |

The complex colors plastics and lacquers in pure red shades of excellent fastness properties.

EXAMPLES 2-7

The procedure of Example 1 is repeated, substituting for 1-(cyanobenzimidazolylmethylene)-3-N-p-nitrophenyliminoisoindoline the following 1-(cyanobenzimidazolylmethylene)-3-N-aryl-iminoisoindolines containing the following radicals as arylimino groups:

Example 3: phenylimino
Example 4: p-tolylimino
Example 5: p-methoxyphenylimino
Example 6: p-chlorophenylimino
Example 7: p-acetylphenylimino In each Example, the same metal complex as above is also obtained in high yield and purity.

EXAMPLE 8

1.09 g (0.005 mole) of 3-acetyl-2,4-dihydroxyquinoline hydrazone and 1.31 g (0.005 mole+5%) of nickel acetate tetrahydrate are suspended in 40 ml of N-methylpyrrolidone and the suspension is heated to 60° C. Then 2.17 g (0.005 mole) of 1-(cyano-p-chlorophenylcarbamoylmethylene)-3-N-p-chlorophenyliminoisoindoline of the formula

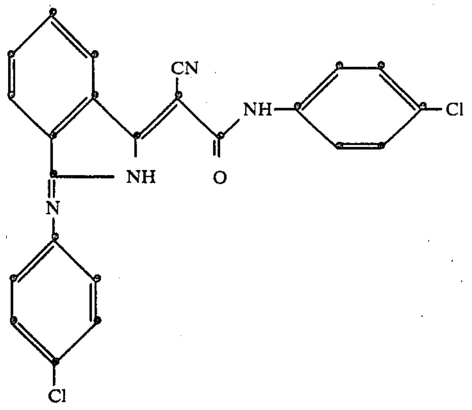

are added and the mixture is heated to 150°-155° C., stirred at the same temperature for 1½ hours and filtered at 80° C. The filter cake is washed with N-methylpyrrolidone and ethanol and dried in vacuo at 80° C., affording 2.22 g (76% of theory) of a red metal complex of the formula

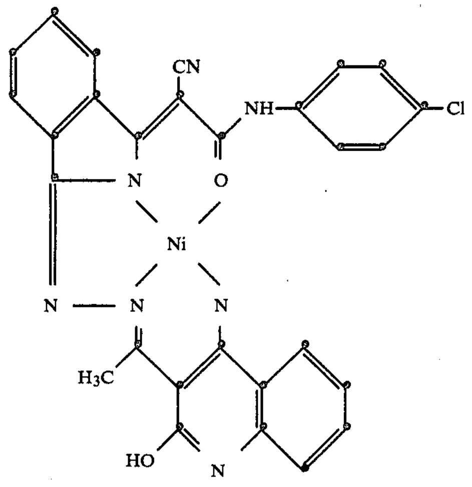

which colors plastics and lacquers in pure red shades of excellent fastness to migration, heat, light, atmospheric influences and migration.

| Microanalysis: $C_{28}H_{17}ClN_6O_3Ni$ (molecular weight 579.65) | C | H | N | Cl | Ni |
|---|---|---|---|---|---|
| % calculated: | 58.02 | 2.96 | 14.50 | 6.12 | 10.13 |
| % found: | 57.70 | 3.30 | 14.30 | 5.90 | 9.70 |

EXAMPLE 9

The procedure of Example 8 is repeated, substituting 1-(cyano-p-chlorophenylcarbamoylmethylene)-3-iminoisoindoline for 1-(cyano-p-chlorophenylcarbamoylmethylene)-3-N-p-chlorophenyliminoisoindoline. A red metal complex of the same composition as in Example 8 is obtained in 60% yield. The colorations obtained with this complex in PVC, lacquers and polyolefins are less pure and of less pronounced fastness to light, atmospheric influences and heat. A similarly deficient metal complex pigment is also obtained by carrying out the procedure of Example 78 of U.S. Pat. No. 4,022,770 and 4,111,947.

EXAMPLE 10

The procedure of Example 8 is repeated, substituting the 3-N-morpholino derivative for 1-(cyano-p-chlorophenylcarbamoylmethylene)-3-N-p-chlorophenyliminoisoindoline. The red nickel complex obtained has the same composition, purity and fastness properties as the product of Example 8.

EXAMPLE 11

The procedure of Example 8 is repeated, substituting the 3-N-piperidino derivative for 1-(cyano-p-chlorophenylcarbamoylmethylene)-3-N-p-chlorophenyliminoisoindoline. The red nickel complex obtained has the same composition and the same lightfastness and resistance to atomospheric influences and heat as the complex of Example 8.

EXAMPLE 12

1.83 g (0.003 mole) of the black 1:1 nickel complex of the formula

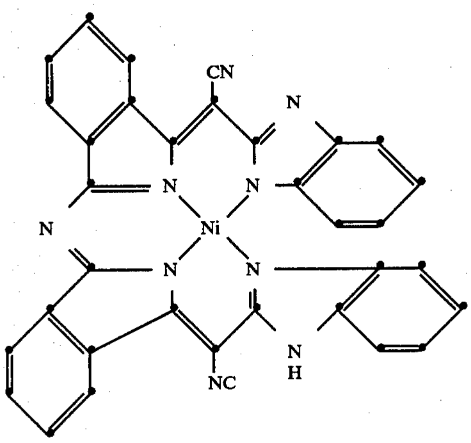

(prepared from 1-(cyanobenzimidazolylmethylene)-3-iminoisoindoline and nickel acetate in accordance with Example 11 of German Offenlegungsschrift No. 2 804 669), 0.78 g (0.003 mole) of nickel acetate tetrahydrate and 1.3 g (0.006 mole) of 3-acetyl-2,4-dihydroxyquinoline hydrazone are suspended in 45 ml of N-methylpyrrolidone. The mixture is heated to about 160° C. and stirred for 2 hours at the same temperature, then filtered at 80° C. The filter cake is washed with N-methylpyrrolidone and ethanol and dried in vacuo at 80° C., affording 1.9 g (59% of theory) of a red metal complex which has the same composition as the product of Example 1 and has excellent fastness properties.

EXAMPLES 13-38

The following table lists further nickel complexes of the formula

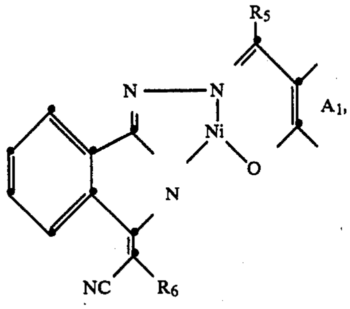

(VI)

(for simplicity's sake, only one of the possible isomeric or tautomeric forms is indicated) which are obtained by condensing a hydrazone of the formula

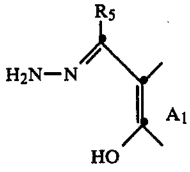

(VII)

wherein $R_5$ and $A_1$ are as defined in columns 2 and 3 respectively, with a 1-methine-3-aryliminoisoindoline of the formula

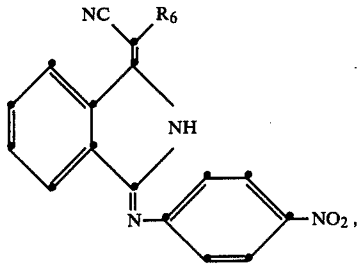

(VIII)

wherein $R_6$ is as defined in column 4, in accordance with the particulars of Examples 1 and 8. The shade obtained in polyvinyl chloride is indicated in column 5.

The starting materials of formula VII are obtained by reacting the corresponding formyl or acetyl compounds with hydrazine hydrate by known methods. The compounds of formula VIII are also obtained by known methods by reacting the corresponding 1-cyanomethylene-3-iminoisoindoline with p-nitroaniline.

TABLE 1
| Example | $R_5$ | $A_1$ 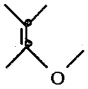 | $R_6$ | Shade in PVC |
|---|---|---|---|---|
| 13 | H | 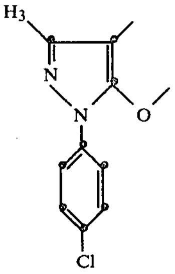 | 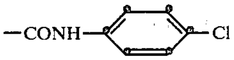 | red |
| 14 | $CH_3$ | 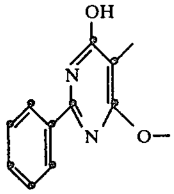 | 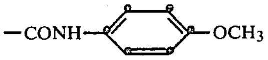 | red |
| 15 | H | 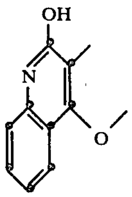 | 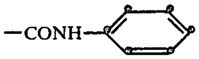 | orange |
| 16 | $CH_3$ | 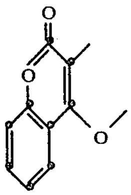 | 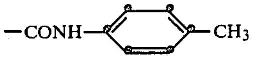 | orange |
| 17 | " | " | 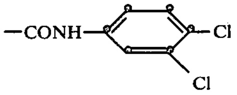 | yellow |
| 18 | " | " | 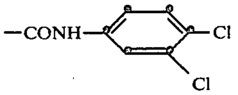 | orange |
| 19 | " | 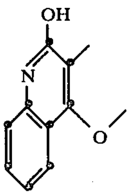 | 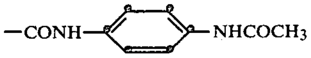 | red |
| 20 | " | " | 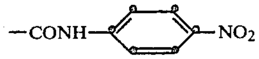 | |

TABLE 1-continued
| Example | $R_5$ | $A_1$ 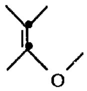 | $R_6$ | Shade in PVC |
|---|---|---|---|---|
| 21 | H | 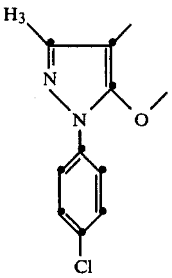 | 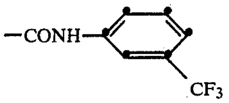 | scarlet |
| 22 | " | " | 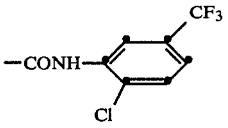 | red |
| 23 | " | " | 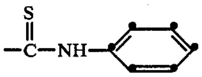 | red |
| 24 | " | " | 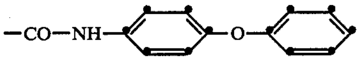 | red |
| 25 | " | " | 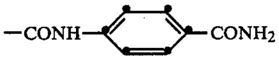 | scarlet |
| 26 | " | " | 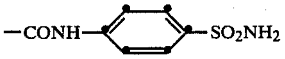 | orange |
| 27 | $CH_3$ | 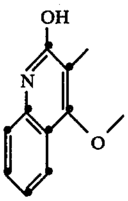 | 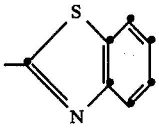 | red |
| 28 | " | 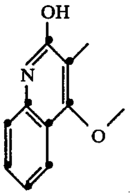 | 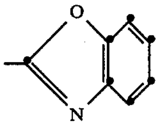 | orange |
| 29 | " | " | 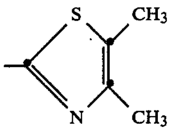 | orange |
| 30 | " | " | 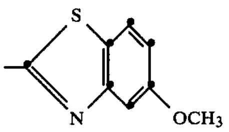 | red |

TABLE 1-continued
| Example | R5 | A1 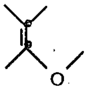 | R6 | Shade in PVC |
|---|---|---|---|---|
| 31 | H | 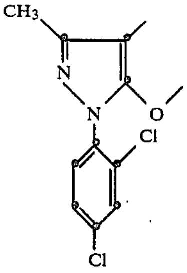 | 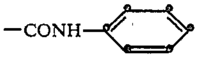 | red |
| 32 | $CH_3$ | 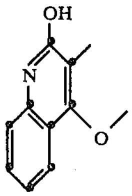 | 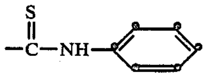 | red |
| 33 | " | " | 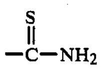 | red |
| 34 | " | 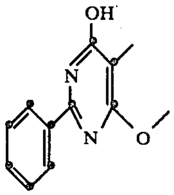 | 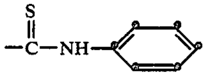 | red |
| 35 | H | 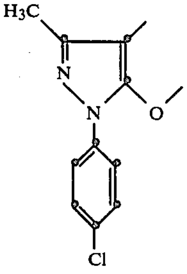 | 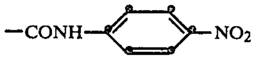 | orange |
| 36 | $CH_3$ | 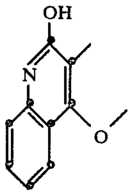 | 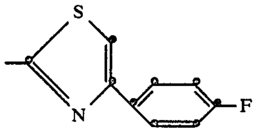 | red |
| 37 | " | " | 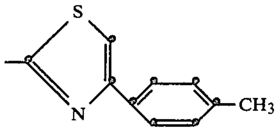 | red |
| 38 | " | " | 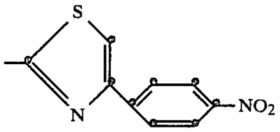 | red |

TABLE 1-continued

| Example | $R_5$ | 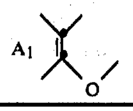 $R_6$ | Shade in PVC |
|---|---|---|---|
| 39 | H | 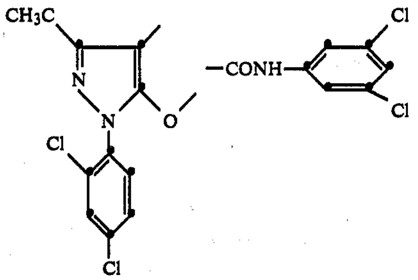 | red |

EXAMPLE 40

17.1 g (0.06 mole) of 1-(cyanobenzimidazolylmethylene)-3-iminoisoindoline (prepared from 1,3-diiminoisoindoline and cyanomethylbenzimidazole) are suspended in 90 ml of dimethyl formamide, and then 7.14 ml (0.072 mole) of n-butylamine are added to the suspension. The mixture is heated to 100° C. and stirred at the same temperature for 3 hours, then cooled to 5° C. and filtered. The filter cake is washed with a small amount of dimethyl formamide and alcohol and dried overnight at 80° C. in vacuo, affording 10.8 g (50.2% of theory) of the compound of the formula

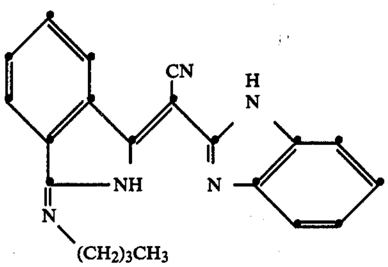

in the form of an orange powder.

| Microanalysis: $C_{21}H_{19}N_5$ (molecular weight 341.4) | | | |
|---|---|---|---|
| calculated: | 73.9% C | 5.61% H | 20.5% N |
| found: | 74.1% C | 5.6% H | 20.6% N |

EXAMPLE 41

The procedure of Example 1 is repeated, substituting the 1-(cyanobenzimidazolylmethylene)-3-N-butyliminoisoindoline derivative (obtained according to Example 40 by reacting 1-(cyanobenzimidazolylmethylene)-3-iminoisoindoline with n-butylamine in dimethyl formamide) for 1-(cyanobenzimidazolylmethylene)-3-N-p-nitrophenyliminoisoindoline. The same metal complex as in Example 1 is obtained in great purity.

EXAMPLE 42

16.25 g (0.05 mole) of 1-(cyano-p-chlorophenylcarbamoylmethylene)-3-iminoisoindoline (prepared from 1,3-diiminoisoindoline and cyanoaceto-p-chloroanilide) are charged into 100 ml of dimethyl formamide. Then 6 ml of a 33% solution of methylamine in alcohol are added and the mixture is stirred for ½ hour at 80°-90° C. and diluted with 30 ml of dimethyl formamide. Further methylamine solution (2 ml) is added and the mixture is allowed to react for a further 5 hours at 90°-100° C. The reaction product is isolated by filtration at 80° C., washed with dimethyl formamide and alcohol and dried overnight in vacuo at 70° C., affording 15.2 g (90.2% of theory) of the compound of the formula

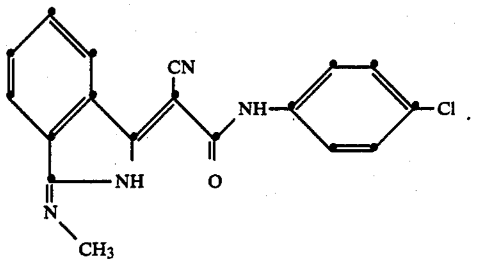

in the form of a yellow powder.

| Microanalysis: $C_{18}H_{13}ClN_4O$ molecular weight | | | | |
|---|---|---|---|---|
| calculated: | 64.20% C | 3.89% H | 16.64% N | 10.53% Cl |
| found: | 64.2% C | 3.8% H | 16.7% N | 10.5% Cl |

EXAMPLE 43

The procedure of Example 8 is repeated, substituting 1-(cyano-o-chlorophenylcarbamoylmethylene)-3-N-methyliminoisoindoline (obtained according to Example 42 from methylamine and 1-(cyano-o-chlorophenylcarbamoylmethylene)-3-iminoisoindoline) for 1-(cyano-p-chlorophenylcarbamoylmethylene)-3-N-p-chlorophenyliminoisoindoline. The same metal complex pigment as in Example 8 is obtained.

EXAMPLE 44

5.46 g (0.139 mole) of 1-(cyano-p-chlorophenylcarbamoylmethylene)-3-imino-5,6-dichloroisoindoline (prepared from 5,6-dichloro-1,3-diiminoisoindoline and cyanoaceto-p-chloroanilide) in 40 ml of dimethyl formamide are treated with 1.7 ml (0.1742 mole) of n-butylamine and the mixture is stirred for 4 hours at 100°-105° C., then cooled to 10° C. and filtered. The filter cake is washed with a small amount of dimethyl formamide and alcohol and dried overnight in in vacuo at 70° C., affording 4.15 g (87.29% of theory) of the compound of the formula

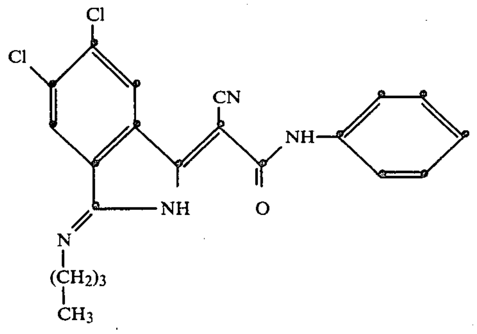

in the form of a yellow powder.

| Microanalysis: $C_{21}H_{17}N_4OCl_3$ (molecular weight 447.8) | | | |
|---|---|---|---|
| calculated: | 56.3% C | 3.83% H | 12.5% N |
| found: | 55.8% C | 4.4% H | 12.9% N |

EXAMPLE 45

2.56 g of the intermediate of Example 44 are added to a suspension, preheated to 60° C., of 1.3 g (0.006 mole) of 3-acetyl-2,4-dioxyquinoline hydrazone and 1.57 g (0.0063 mole) of nickel acetate tetrahydrate in 40 ml of N-methylpyrrolidone. The mixture is heated to 150° C. and stirred for 2 hours at the same temperature, then filtered at 80° C. The filter cake is washed with N-methylpyrrolidone and ethanol and dried at 80° C. in vacuo, affording 2.12 g (54.5% of theory) of a red pigment of the following structure (only one of the possible isomeric or tautomeric forms is indicated)

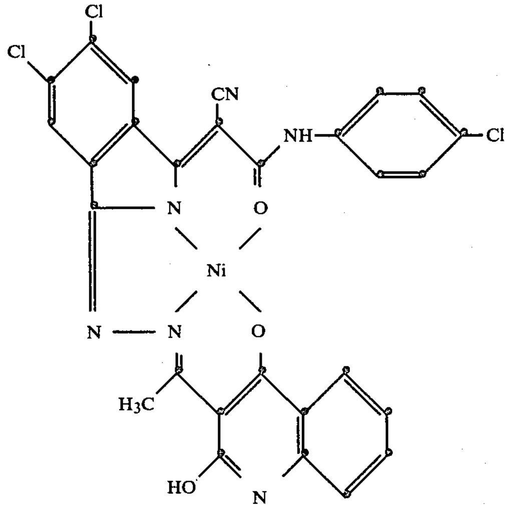

which colors plastics and lacquers in pure red shades of excellent fastness to heat, light, atmospheric influences and migration.

| Microanalysis: $C_{28}H_{15}Cl_3N_6O_3Ni$ (molecular weight 648.5) | | | | | |
|---|---|---|---|---|---|
| calculated: | 51.86% C | 2.33% H | 16.40% Cl | 12.96% N | 9.05% Ni |

-continued

| Microanalysis: $C_{28}H_{15}Cl_3N_6O_3Ni$ (molecular weight 648.5) | | | | | |
|---|---|---|---|---|---|
| found: | 51.8% C | 2.8% H | 15.8% Cl | 13.1% N | 9.10% Ni |

EXAMPLES 46-50

The procedure of Example 8 is repeated, using the following indolines of the formula

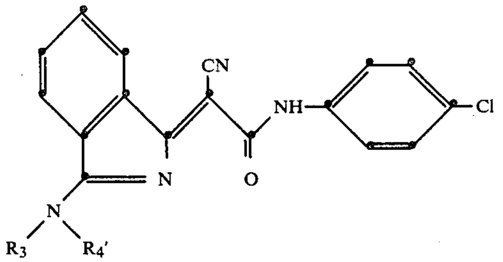

instead of 1-(cyano-p-chlorophenylcarbamoylmethylene)-3-N-p-chlorophenyliminoisoindoline:

Example 46

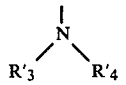

Example 47

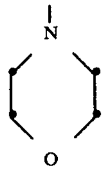

Example 48

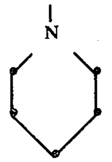

Example 49

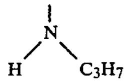

Example 50

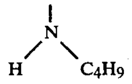

The same metal complex as in Example 8 is obtained in high yield and purity.

EXAMPLE 51

A laboratory kneader having a capacity of 250 parts by volume is charged with 25 parts of the pigment obtained in Example 8, 100 parts of finely ground sodium chloride and 30 parts of diacetone alcohol. The mixture is kneaded for 5 hours with cooling and then discharged into 4000 parts by volume of water. Sodium chloride and diacetone alcohol go into solution and the pigment precipitates. The suspension is filtered and the filter cake is washed thoroughly with water and dried in a vacuum drying cabinet at 80° C.

EXAMPLE 52

65 parts of stabilised polyvinyl chloride, 35 parts of dioctyl phthalate and 0.2 part of the pigment obtained in Example 51 are stirred together and then rolled for 7 minutes at 160° C. on a two-roll calender to produce an orange-red sheet of very good fastness to light and migration.

EXAMPLE 53

10 g of titanium dioxide and 2 g of the pigment obtained in Example 8 are ground for 48 hours in a ball mill with 88 g of a mixture of 26.4 g of coconut alkyd resin, 24 g of melamine/formaldehyde resin (50% solids content), 8.8 g of ethylene glycol monomethyl ether and 28.8 g of xylene. The resultant lacquer is sprayed onto an aluminium sheet, predried for 30 minutes at room temperature, and then stoved for 30 minutes at 120° C. A red finish of very good fastness to overspraying, light, and atmospheric influences is obtained.

EXAMPLE 54

4 parts of the finely dispersed pigment of Example 51 are stirred into 20 parts of solvent of the following composition: 50 parts of Solvesso 150 (mixture of aromatic hydrocarbons), 15 parts of butylacetate, 5 parts of Exkin II (ketoxime-based levelling agent), 25 parts of methyl isobutyl ketone, 5 parts of silicone oil (1% in Solvesso 150). After complete dispersion has been attained (in about 15-60 minutes, depending on the type of stirrer), the binders are added, namely 48.3 parts of Baycryl L 530 (acrylic resin; 51% in xylene/butanol 3:1) and 23.7 parts of Maprenal TTX (melamine resin; 55% in butanol).

The batch is briefly homogenised and the resultant lacquer is then applied by conventional methods, such as spraying or dipping or—particularly for the continuous coating of sheet metal—by the coil-coating method, and stoved (30 minutes at 130° C.). The red finishes obtained are distinguished by very good levelness, high gloss and excellent dispersion of the pigment, as well as by excellent fastness to atmospheric influences.

EXAMPLE 55

The procedure of Example 51 is repeated, except that 2.78 parts of Staybelite Resin (available from HERCULES) are added to the kneading stock. The resultant product is a pigment with a 10% resin content which can be more easily incorporated and having improved dispersibility.

What is claimed is:

1. A process for the manufacture of a 1:1 metal complex of an azine of formula I (I)

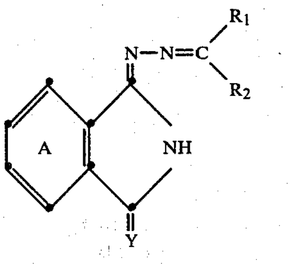

wherein the ring A is unsubstituted or is substituted by 2 to 4 chlorine atoms, by 1 to 2 alkyl or alkoxy groups having each 1 to 4 carbon atoms, by a phenoxy, by phenyl, by nitro, by benzoylamino or by a $C_{2-6}$-alkanoylamino group, $R_1$ is a hydrogen atom or a methyl group, $R_2$ is a radical selected from the group consisting of

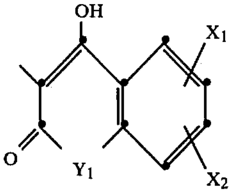 , 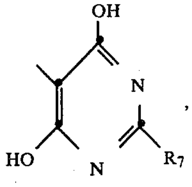 ,

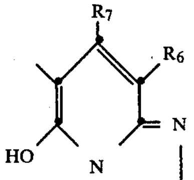 , 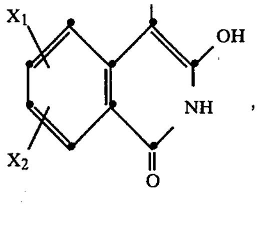 ,

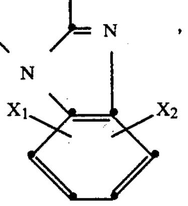

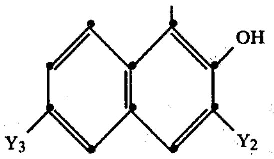 and 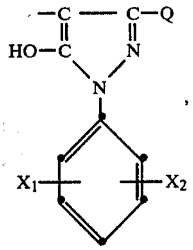 ,

Y is the radical of a heteroaryl amine selected form the group consisting of 2-aminothiophene, 2-aminothiazole, 2-amino-5-nitrothiazole, 2-amino-5-methylsulfonylthiazole, 2-amino-5-cyanothiazole, 2-amino-4-methyl-5-nitrothiazole, 2-amino-4-methylthiazole, 2-amino-4-phenylthiazole, 2-amino-4-(4'-chloro)-phenylthiazole, 2-amino-4-(4'-nitro)-phenylthiazole, 2-aminopyrazole, 3-amino-1-phenylpyrazole, 3-aminoindazole, 5-methylsulfonyl-2-aminothiazole, 5-benzoyl-2-aminothiazole, 4-aminoimidazole, 4,5-dicyano-2-aminoimidazole, 4,5-diphenyl-2-aminothiazole, 2-amino-3,4-thiadiazole, 2-amino-3,5-thiadiazole, 3-amino-1,2,4-triazole, 2-amino-3,4-oxadiazole, 3-aminopyridine, 2-aminopyridine-N-oxide, 2-amino-benzthiazole, 2-amino-6-chlorobenzthiazole, 2-amino-6-methylbenzthiazole, 2-amino-6-methoxybenzthiazole, 2-amino-6-chloro-4-nitrobenzthiazole, 2-amino-6-bromo-4-cyanobenzthiazole, 2-amino-6-cyano-4-methylbenzthiazole, 2-amino-6-methyl-4-nitrobenzthiazole, 2-amino-6-methoxy-4-nitrobenzthiazole, 2-amino-6-butoxy-4-chlorobenzthiazole, 2-amino-4-chloro-5-methoxybenzthiazole, 2-amino-4-bromo-6-methoxybenzthiazole, 2-amino-4,6-dichlorobenzthiazole, 2-amino-4,6-dibromobenzthiazole, 2-amino-4-methyl-6-(trifluoromethyl)-benzthiazole, 2-amino-4-methyl-6-propionylbenzthiazole, 2-amino-4-chloro-6-methylsulfonyl-benzthiazole, 3-aminobenzisothiazole, 3-amino-5-chloro-benzisothiazole, 2-amino-3-cyanotetrahydrobenzthiaphene, 2-amino-benzimidazole, 2-amino-6-chlorobenzimidazole, 2-amino-6-bromo-benzimidazole, 2-amino-6-methylbenzimidazole, 2-amino-6-methoxy-benzimidazole, 2-amino-6-ethoxybenzimidazole, 2-amino-6-methylsulfonyl-benzimidazole, 2-amino-6-acetylaminobenzimidazole, 2-aminopyridine, diaminophthalazine, 2-amino-4-hydroxyquinoline, 2,6-diaminopyridine and 2-amino-4,5-dimethyl-thiazole, or Y is a group of the formula

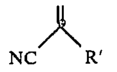

R' is —$CONH_2$, —$CSNH_2$ or a radical selected from the group consisting of

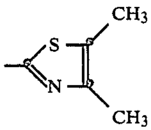
,
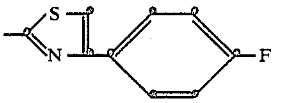
,
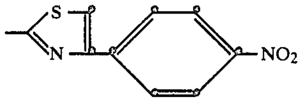
,
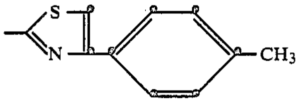
,
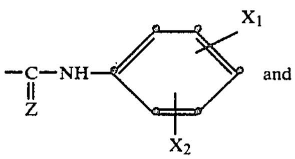
and
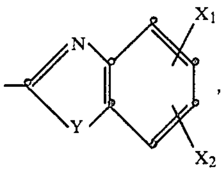
, $Y_1$ is —O—, —S— or —NH—, $Y_2$ is a hydrogen atom, a carboxyl or carbamoyl group, an alkoxycarbonyl or alkylcarbamoyl group containing 2 to 6 carbon atoms, a phenylcarbamoyl group which is unsubstituted or substituted in the phenyl moiety by halogen atoms, alkyl or alkoxy groups containing 1 to 4 carbon atoms, $Y_3$ is a hydrogen or a halogen atom, a methoxy, nitro or cyano group, $X_1$ is a hydrogen, chlorine or bromine atom, a nitro, trifluoromethyl, carbamoyl or sulfamoyl group, an alkyl, alkoxy or alkylsulfamoyl group of 1 to 4 carbon atoms, an alkanoylamino, alkylcarbamoyl or alkoxycarbonyl group of 2 to 6 carbon atoms, a phenoxy, phenylcarbamoyl or phenylsulfamoyl group which is unsubstituted or substituted by chlorine or bromine atoms or methyl groups, $X_2$ is a hydrogen, chlorine or bromine atom, an alkyl or alkoxy group of 1 to 4 carbon atoms, $R_6$ is a cyano, carbamoyl or alkoxycarbonyl group of 2 to 6 carbon atoms, $R_7$ is a hydrogen atom, an alkyl group of 1 to 4 carbon atoms, a phenyl or hydroxy group, Q is a methyl group or an alkoxycarbonyl group containing 2 to 5 carbon atoms or a carbamoyl group, Z is —O— or —S— and V is —O—, —S— or —NH—, which process comprises reacting a compound of the formula II

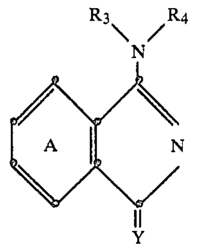
(II)

wherein $R_3$ is a hydrogen atom or an alkyl group having 1 to 6 carbon atoms, and $R_4$ is an alkyl group having 1 to 6 carbon atoms, or

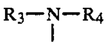

is the radical of the formula

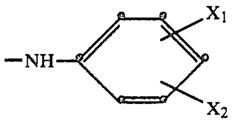

wherein $X_1$ and $X_2$ are as defined above, or $R_3$ and $R_4$ together with the N-atom to which they are attached form a pyrrolidino, piperidino or morpholino radical, with a hydrazone of the formula II

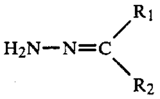
(III)

in the presence of a transition metal donor and in a polar organic solvent, at temperatures above 100° C., Y, $R_1$ and $R_2$ having the meanings given under formula I, and the ring A being as defined under formula I.

2. A process according to claim 1 where in the azine of formula I the ring A is unsubstituted.

3. A process according to claim 1 wherein Y is a group

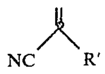

where $R^1$ is as defined in claim 1.

4. A process according to claim 1, wherein the starting material is a compound of the formula (II), in which Y is a radical of the formula

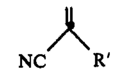

wherein R′ is a carbamoyl or thiocarbamoyl group or a group of the formula

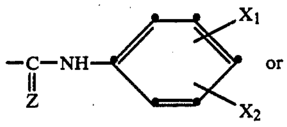 or 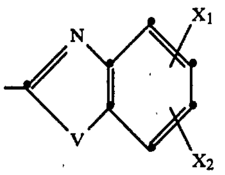

wherein Z is an oxygen or a sulfur atom, $X_1$ is a hydrogen, chlorine or bromine atom, a nitro, trifluoromethyl, carbamoyl or sulfamoyl group, an alkyl, alkoxy or alkylsulfamoyl group of 1 to 4 carbon atoms, an alkanoylamino, alkylcarbamoyl or alkoxycarbonyl group of 2 to 6 carbon atoms, a phenoxy, phenylcarbamoyl or phenylsulfamoyl group which is unsubstituted or substituted by chlorine or bromine atoms or methyl groups, and $X_2$ is a hydrogen, chlorine or bromine atom, an alkyl or alkoxy group of 1 to 4 carbon atoms, and V is O, S, or NH.

5. A process according to claim 1, wherein the starting material is a compound of the formula (II), in which

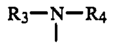

is the radical of the formula

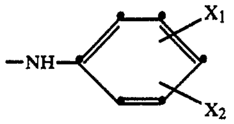

wherein $X_1$ and $X_2$ are as defined in claim 1.

6. A process according to claim 1, wherein the starting material is a hydrazone of the formula

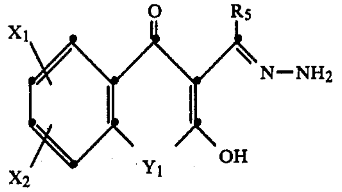

wherein $R_5$ is hydrogen or methyl and $Y_1$ is O, S or NH, and $X_1$ and $X_2$ are as defined in claim 1.

7. A process according to claim 1, wherein the metal donor is a nickel salt.

8. A process according to claim 1, wherein dimethyl formamide or N-methylpyrrolidone is used as polar solvent.

9. A process according to claim 1, wherein the reaction is carried out in the temperature range from 100° to 200° C.

* * * * *